United States Patent [19]

Herwig et al.

[11] Patent Number: 4,504,688

[45] Date of Patent: Mar. 12, 1985

[54] PROCESS FOR THE PREPARATION OF PURE ALKYL TERT-ALKYL ETHERS AND HYDROCARBON RAFFINATES WHICH ARE LARGELY FREE FROM ISOOLEFINS AND FROM ALKANOLS

[75] Inventors: Jens Herwig, Cologne; Hans-Volker Scheef; Bernhard Schleppinghoff, both of Dormagen; Peter M. Lange, Leverkusen, all of Fed. Rep. of Germany

[73] Assignees: EC Erdolchemie GmbH, Cologne; Bayer Aktiengesellschaft, Leverkusen, both of Fed. Rep. of Germany

[21] Appl. No.: 587,094

[22] Filed: Mar. 7, 1984

Related U.S. Application Data

[63] Continuation of Ser. No. 385,226, Jun. 4, 1982, abandoned.

[30] Foreign Application Priority Data

Jun. 19, 1981 [DE]  Fed. Rep. of Germany ....... 3124293

[51] Int. Cl.$^3$ .................... C07C 41/05; C07C 41/36
[52] U.S. Cl. ...................................... 568/697; 568/699
[58] Field of Search ................................ 568/697, 699

[56] References Cited

U.S. PATENT DOCUMENTS

| | | | |
|---|---|---|---|
| 3,021,274 | 2/1962 | Radzitzky | 568/697 |
| 3,726,942 | 4/1973 | Louder | 568/697 |
| 4,322,565 | 3/1982 | Dotson et al. | 568/697 |
| 4,371,718 | 2/1983 | Hutson, Jr. | 568/697 |

FOREIGN PATENT DOCUMENTS

| | | | |
|---|---|---|---|
| 50-10561 | 4/1975 | Japan | 568/699 |
| 56-111050 | 9/1981 | Japan | 568/917 |

*Primary Examiner*—Howard T. Mars
*Attorney, Agent, or Firm*—Sprung, Horn, Kramer & Woods

[57] ABSTRACT

A process for the preparation of pure alkyl tertiary alkyl ethers and hydrocarbon raffinates which are substantially free from tertiary olefins and alkanols. An alkanol and a hydrocarbon mixture containing at least one tertiary olefin are contacted with the alkanol being present in a stoichiometric excess. The reaction product is removed from the reaction zone and excess alkanol in the reaction product or a partial stream thereof is absorbed on a synthetic ion exchanger containing groups which exchange cations or anions or mixtures of such ion exchangers. After absorption of at least a portion of the alkanol on the synthetic ion exchanger, the alkanol is desorbed by contacting the same with a hydrocarbon mixture containing at least one tertiary olefin.

24 Claims, 3 Drawing Figures

PROCESS FOR THE PREPARATION OF PURE ALKYL TERT-ALKYL ETHERS AND HYDROCARBON RAFFINATES WHICH ARE LARGELY FREE FROM ISOOLEFINS AND FROM ALKANOLS

This is a continuation of application Ser. No. 385,226, filed June 4, 1982, now abandoned.

BACKGROUND OF THE INVENTION

The present invention relates to a process for the preparation of pure alkyl tert.-alkyl ethers and hydrocarbon raffinates which are largely free from isoolefins and from alkanols, by reaction, on acid ion exchangers, of alkanols and hydrocarbon mixtures containing at least one tert.-olefin, and absorptive removal of excess alkanol from the reaction mixture.

Alkyl tert.-alkyl ethers, such as methyl tert.-butyl ether (MTBE) and tert.-amyl methyl ether (TAME), are used, for example, as fuel additives for carburettor-type engines for improving the octane number, and as solvents and extracting agents which, for example, form hardly any peroxides, in contrast to many other ethers. In addition, the alkyl tert.-alkyl ethers are suitable starting materials for the preparation, via ether cleavage, of pure tert.-olefins based on these ethers.

The reaction of tert.-olefins and alkanols on acid ion exchangers to give alkyl tert.-alkyl ethers is known (German Pat. No. 1,224,294). Since this reaction is very selective, mixtures of tertiary olefins with other hydrocarbons, as produced, for example, in thermal or catalytic crackers, are particularly suitable starting materials.

The closeness of approach of the tertiary olefin conversion to the quantitative conversion depends on the type of tertiary olefin and on the choice of the alkanol. In this respect, the conversions of i-butene, for example from the $C_4$-raffinate of thermal cracking (mostly called $C_4$-raffinate I), are particularly high, whilst the conversions of i-amylene and other tertiary olefins of increasing carbon number are lower under comparable conditions. Conversion and yield can be improved by special measures in carrying out the reaction during the preparation of MTBE, such as the choice of 2 or more successive reaction stages (German Offenlegeschrift No. 2,521,964, German Offenlegeschrift No. 2,706,465, and German Offenlegeschrift No. 2,944,914), or the use of a large excess of methanol (German Offenlegeschrift No. 2,853,769).

Particularly in the case of $C_4$-raffinates, a high i-butene conversion is desirable, since, for further utilization of the i-butene-free $C_4$-raffinate, the residual content of i-butene should be below 2% by weight, if possible even below 1 or below 0.5% by weight. This specification is necessary when, for example, maleic acid anhydride, methyl ethyl ketone, but-1-ene or octenes are to be prepared, by dimerization, from these residual mixtures, mostly called $C_4$-raffinate II. For further use in this respect, care must also be taken to ensure that alkanol is no longer present in the $C_4$-raffinate II. Thus, achieving an "on-specification" raffinate and a pure ether, such as, for example, in the processes for the production of MTBE and TAME, involves special requirements.

However, owing to azeotropic effects, it has been found that the two required aims, namely a methanol-free ether and also a methanol-free $C_4$-raffinate II or $C_5$-raffinate, cannot be achieved by simple distillation (see German Offenlegeschrift No. 2,802,198, page 3, paragraph 3). $C_4$- and $C_5$-hydrocarbons in particular form methanol-containing azeaotropes which, when i-butene/i-amylene are etherified together, for example from hydrocarbons which contain various $C_4$- and $C_5$- olefins and -alkanes, made an exact $C_4/C_5$-separation impossible, since, together with the methanol, $C_5$-hydrocarbons also occur in the $C_4$-top product of the debutanizing column.

An azeotrope is also formed, for example, by MTBE and methanol. A water wash has been proposed (German Offenlegeschrift No. 2,246,004 and U.S. Pat. No. 3,726,942) as a useful method for removing the methanol from the $C_4$-raffinate II and from the MTBE/methanol azeotrope. Additional suitable methods for separating the MTBE/methanol azeotrope are extractive distillation using dimethylsulphoxide (Japanese Preliminary Published Application 73-00509) or using pentane (U.S. Pat. No. 3,940,450) or distillative separation of the azeotrope from pure MTBE using relatively high pressures of 5 to 20 bar (German Offenlegeschrift No. 2,629,769).

French No. 7,903,416 describes the separation of methanol from the $C_4$-raffinate II as an absorption process on a molecular sieve, with subsequent desorption by hot nitrogen and recovery of the methanol by condensation from the $N_2$ stream.

The stated measures for the purification of the reaction products and raffinates require substantially higher capital costs than the actual etherification reaction, and also require a large additional energy demand, relative to the total process.

Furthermore, U.S. Pat. No. 3,409,691 discloses the separation of an amount of 500 ppm of secondary butanol from n-hexane on macroporous cation exchangers in the $Na^+$ form. To regenerate the cation exchanger, the butanol is displaced by methanol and the methanol is in turn removed again by heating the cation exchangers at 110° C. in vacuo overnight.

Furthermore, German Offenlegeschrift No. 2,027,066 describes the possibility of removing methanol from water (1 g of methanol per 1 l of water) with the aid of a styrene/divinylbenzene polymer containing nitro groups. The adsorptive power in this case is 18 g of methanol per kg of adsorbent. The adsorbent is regenerated by means of steam distillation.

SUMMARY OF THE INVENTION

A process for the preparation of pure alkyl tert.-alkyl ethers and hydrocarbon raffinates largely free from tert.-olefins and from alkanols by reaction, on acid cation exchangers, of an alkanol and hydrocarbon mixtures containing at least 1 tert.-olefin has now been found, which is characterized in that excess, unreacted alkanol is removed from the product mixture emerging from the reaction zone, or from its part streams produced in the working-up, by absorption on an absorber resin, and the alkanol to be fed into the reaction zone is taken at least partially from the absorber resin charged with this alkanol, by means of desorption with the aid of the hydrocarbon mixture containing at least 1 tert.-olefin.

The absorber resin employed for the absorption and desorption is divided into at least 2 layers for carrying out the process according to the invention, of which layers at least one is employed for absorption in a largely alkanol-free state, whilst another absorber layer, already charged with the alkanol, in the stream of the starting hydrocarbons for the process according to the invention, is switched to desorption. The two absorber layers mentioned are switched over in good time to be sure of avoiding the alkanol charge reaching such a level that the alkanol "penetrates" through the absorber layer, and so that the layer which is now charged is switched into the stream of the starting hydrocarbons and the absorber layer previously free from alkanol is available for the separation of the alkanol from the end products. It is of course also possible to employ more than 2 absorber layers, a second safety layer being connected behind the first absorption layer. In this case, the alkanol capacity of the first absorber layer can be fully utilized, since alkanol which partially "penetrates" through the first layer is collected in the second layer. The "penetration" can be detected in a known manner, for example by gas chromatographic measurement or infrared detectors in the exit product stream. After this first absorption layer has been charged, this absorber unit is switched over to the starting hydrocarbon stream, for desorption. The previous safety absorption layer now takes the place of this first absorption layer, and a freshly regenerated absorber layer takes the place of the previous safety absorption layer.

The total process of the process according to the invention can be described, for example, by the following general equation:

| Mixture A (tert.-olefin, other olefins, alkanes, aromatics) | + | Absorber containing alkanol (for desorption) | + | Alkanol, stoichiometric ratio to tert.-olefin |
|---|---|---|---|---|
| →alkyl tert.-alkyl ether | + | Absorber with alkanol excess | + | Mixture B (other olefins, alkanes and aromatics) |

From this equation, it can be seen that a stoichiometric amount of alkanol with respect to the tert.-olefin is fed in, but that, as a consequence of the desorption of the alkanol from the absorption resin, excess alkanol, relative to the amount of tert.-olefin, is present in the reactor. The additional amount of fresh alkanol can also be chosen to be superstoichiometric in order to increase the alkanol excess still further. By this means, a quantitative conversion of the tert.-olefin is achieved. This alkanol excess in the reactor is from 1 to 400% by weight above the amount of alkanol required for quantitative conversion of the tert.-olefin.

When, particularly in the case of tert.-olefins with a relatively high C atom number, the reaction equilibrium leads to incomplete conversion of the tert.-olefin to the relevant ether, for example only to 75–95% of the complete conversion, it can be economically meaningful to employ less than 100 mol% of alkanol per 100 mol% of tert.-olefin. In general, higher amounts of alkanol hardly affect the equilibrium mentioned and lead to an unacceptably high expense in recovering the alkanol. However, an amount of alkanol above that required for achieving the equilibrium mentioned is preferably employed. For example, if the equilibrium of conversion of a tert.-olefin into the relevant ether is at about 80 mol% of the total tert.-olefin present, it can be meaningful to employ about 90 mol% of alkanol, relative to the number of mols of tert.-olefin. The residual 10 mol%, approximately, of alkanol can then be separated off according to the invention.

An aliphatic, straight-chain or branched alcohol having 1 to 8, preferably 1 to 4, particularly preferably 1 or 2, carbon atoms, may be mentioned as an alkanol for the process according to the invention. Examples of these are methanol, ethanol, propanol, isopropanol, butanol, isobutanol, straight-chain or branched pentanol, hexanol, heptanol or octanol.

All hydrocarbon streams which contain at least 1 tert.-olefin are suitable as the mixture A of the above equation, and therefore as the starting stream for the etherification according to the invention. Such tert.-olefins have, for example, 4 to 10, preferably 4 to 6, particularly preferably 4 or 5, carbon atoms, such as i-butene, tert.-pentene, tert.-hexene, tert.-octene or tert.-decene. Starting streams which contain at least one of the tert.-olefins mentioned and can thus be employed according to the invention can be, for example, a crude $C_4$-cut or a $C_4$-raffinate I (after butadiene extraction) from a thermal cracker or an FCC crude product stream from a fluid catalytic cracker (FCC), or a $C_4/C_5$-LCC stream from a catalytic cracker (LCC=light catalytic cracker). The FCC crude product stream can of course previously have been divided into a $C_4$-FCC stream and a $C_5$-FCC stream. A $C_5$ stream of a thermal cracker, for example light ends in the distillation during the production of aromatics, is also suitable. Further suitable product streams are those of an n-butene skeleton isomerization or an i-butane dehydrogenation, in which i-butene is present. When hydrocarbon mixtures containing more than 1 tert.-olefine are employed, mixtures of several alkyl tert.-alkyl ethers can be formed. These can be used as mixtures and also, after separation by distillation, in the form of their individual components.

Such mixtures A contain, for example, 0.5 to 80% by weight of one or more tert.-olefins.

For the absorption and desorption according to the invention, the substance mixture to be treated is always present as a liquid phase. Thus, the absorption and desorption of the alkanol can be carried out, without an energy-consumptive phase change, together with the etherification which is also carried out in the liquid phase. In the case in which a part stream of etherification products which is to be freed from alkanol is produced as a top product by distillative separation, this stream is condensed before the alkanol absorption, an operation which would have been necessary for further manipulation, in any case. To establish a liquid phase, particularly in the case of lower-boiling mixtures or constituents thereof, the process is carried out at lower temperatures and/or higher pressures. However, in the case of higher-boiling constituents, the process can also be carried out at higher temperatures or lower pressures.

The absorption of the excess alkanol can be carried out, for example, in the range from 0° to 60° C., preferably 15°–35° C. For example 0.1 to 20 bar, preferably 1 to 15 bar, can be chosen as the pressure. The desorption of the alkanol with the aid of the starting gas stream can proceed, basically, under the same conditions as for the absorptions. This applies in particular when the starting stream containing the tert.-olefin is substantially greater than the exit gas stream without this tert.-olefin. In general, it is desirable to keep the desorption time shorter than the absorption time. In this case the desorption is carried out, for example, at a temperature of 20° to 100° C., preferably 30 to 60° C. For example 3 to 30 bar, preferably 5 to 15 bar, may be mentioned as the pressure for the desorption.

By suitable choice of the temperatures and pressures for the absorption and desorption within the ranges mentioned, the rate of desorption is adjusted to be 0.5 to 10 times, preferably 1.5 to 4 times, the value of the rate of absorption. A higher rate of desorption can be achieved, for example, by establishing a higher temperature compared with the absorption.

For example, in the case in which an alkanol-free part stream (ether or residual gas) is initially separated off from the etherification mixture, only the remaining alkanol-containing part stream must be fed to the alkanol removal via the absorber resin. In this case, the starting stream is greater, for example owing to the presence of the tert.-olefin, than the remaining part stream which has been described, and produces a greater WHSV desorption than the remaining part stream in the absorption. In addition, it has surprisingly been found that the rate of desorption for the alkanol increases with the content of tertiary olefins in the flushing stream, so that to establish a higher rate of desorption the choice of a higher temperature may be unavoidable. Particularly for continuous operation of the process according to the invention, it is thereby possible to ensure that the desorption time is shorter than the absorption time, and a fresh, regenerated absorber layer is thus always available when the absorption filter has been exhausted. The absorber layer throughput for absorption and for desorption is chosen within the range of an hourly space velocity WHSV (weight hourly space velocity) of 0.1 to 100, preferably of 0.5 to 20, particularly preferably of 1 to 15, kg of gas stream per kg of absorber per hour. It is advantageous to choose a higher WHSV for the desorption than for the absorption. The desorption can be effected at the same low temperature as the absorption and still be more rapid than the absorption, favoring a continuous procedure. This choice of lower temperatures ensures, in particular, an energy-saving mode of operation.

The product mixture emerging from the reaction zone, or a part stream produced in the working-up, can have an alkanol concentration between 0.01 and 90% by weight, preferably from 1 to 60% by weight, relative to the total stream.

Synthetic ion exchangers containing groups which exchange cations or anions, or mixtures of such ion exchangers, may be mentioned as examples of an absorber resin for the process according to the invention.

Such ion exchangers have, for example, a matrix based on crosslinked styrene polymers. Divinylbenzene, trivinylbenzene or trivinylcyclohexane in an amount of about 0.3–80% by weight, preferably 1–65% by weight, particularly preferably 2–50% by weight, relative to the total weight of the comonomers, may be mentioned as examples of crosslinking agents. However, the matrix can also be a phenol/formaldehyde condensate, a methacrylic or acrylic resin, or an epichlorohydrin/polyamine condensate, in a crosslinked form in each case. Such crosslinked matrices can be employed in the gelatinous or the macroporous form.

The following may be mentioned as examples of exchanging groups on these matrices: sulphonic acid groups, phosphonic acid groups and carboxyl groups, in the $H^+$ form or in the metal ion form in each case. In this connection, metal ions from all groups of the periodic table (Mendeleev) may be mentioned, for example $Li^+$, $Na^+$, $K^+$, $Rb^+$, $Cs^+$, $NH_4^+$, $Cu^+$, $Ag^+$, $Mg^{++}$, $Ca^{++}$, $Ba^{++}$, $Zn^{++}$, $Al^{+++}$, $Sn^{++}$, $Pb^{++}$, $Ce^{4+}$, $UO_2^{++}$, $Cr^{+++}$, $Co^{++}$, $Ni^{++}$, $Fe^{++}$, $Fe^{+++}$ or $Pd^{++}$. The following may preferably be mentioned: $Na^+$, $K^+$, $NH_4^+$, $Ca^{++}$ or $Fe^{+++}$, particularly preferably $Na^+$.

Further exchanging groups can, for example, be: $-NR_3^+$, such as $-N(CH_3)_3^+$ or $-N(CH_3)_2CH_2CH_2OH^+$, or $-NR_2$, such as $-N(CH_3)_2$, as well as N-oxide groups. Such N-containing groups can contain, for example, the OH, Cl or $SO_4$ ion as the exchangeable counter ion. Anion exchangers of this type containing the group $-N(CH_3)_3^+$ are known to one skilled in the art as those of type I, and anion exchangers containing the group $-N(CH_3)_2CH_2CH_2OH^+$ are known to one skilled in the art as those of type II.

Ion exchangers of the types described have, for example, total ion exchange capacities of about 0.5–6 equivalents/l of resin. Such resins and their preparation processes have been known for a long time (Ion Exchange, F. Helfferich, McGraw-Hill Book Company, New York 1962; Ullmanns Enzyklopädie der technischen Chemie (Ullmann's Encyclopaedia of Industrial Chemistry), 4th edition, volume 13, pages 279 et seq., Verlag Chemie 1977).

Examples of resins which can be employed according to the invention are: gelatinous styrene/divinylbenzene resins containing sulphonic acid groups, macroporous styrene/divinylbenzene resins containing sulphonic acid groups, gelatinous or macroporous (meth)-acrylic acid/divinylbenzene resins containing carboxyl groups, gelatinous or macroporous styrene/divinylbenzene anion exchangers of type I or II, macroporous or gelatinous styrene/divinylbenzene resins containing $-N(CH_3)_2$ groups, slightly basic, macroporous resins of the acrylamide/divinylbenzene type, strongly basic, macroporous resins of the acrylamide/divinylbenzene type or cross-linked phenol/formaldehyde resins containing sulphonic acid groups. The list is not complete and does not represent a restriction to the resins mentioned. Many of these resins are commercial products of various manufacturers.

BRIEF DESCRIPTION OF DRAWINGS

The process according to the invention can be carried out in many variants, which can be illustrated, for example, with the aid of the attached drawings, all of which are flow diagrams showing variations of the process of the invention.

DESCRIPTION OF SPECIFIC EMBODIMENTS

Figure 1:
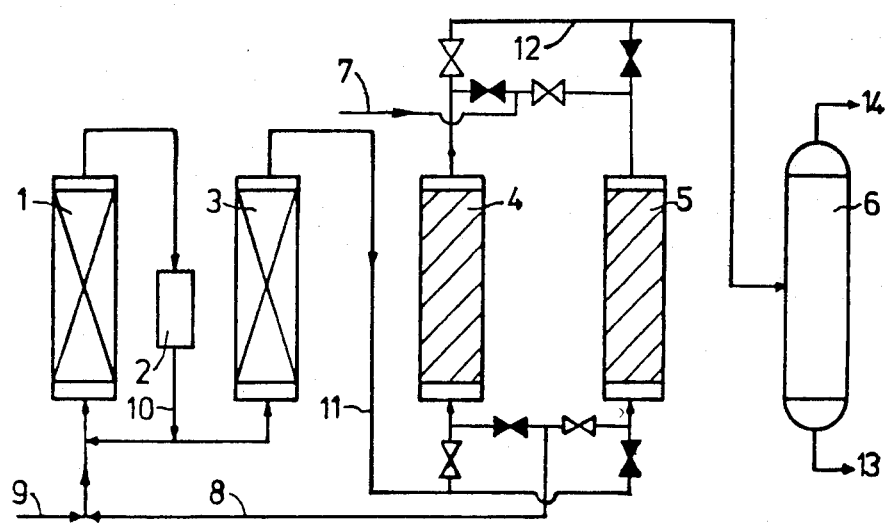

In FIG. 1, the positions 1 and 3 denote two etherification reactors in which the etherification catalyst is arranged in a fixed bed. In general, a cation exchanger which is known in itself, in the $H^+$ form, is employed as the etherification catalyst, for example a styrene/divinylbenzene polymer which carries sulphonic acid groups. The etherification reactions in the example of FIG. 1 are operated such that only a part of the etherification is carried out in 1, whilst this reaction is completed in 3. A cooler 2 is used to conduct away the positive heat of reaction. The reaction mixture leaving the cooler 2 is divided up, and a part of it is further fed to 1, whilst the other part is further fed to 3 to complete the reaction. The reacted reaction mixture, which is largely free of tert.-olefins after the etherification, is now passed into an absorber layer 4 for the removal of alkanol. The reaction mixture 12, which leaves the absorber layer 4 and is freed from alkanol, is now fed into a so-called debutanizing column 6, in which it is separated into the desired pure alkyl tert.-alkyl ether 13 as the bottom product and a hydrocarbon raffinate 14 which is largely free from isoolefins and from alkanols, as the top product. The starting stream 7 containing the isoolefin is passed over an absorber layer 5 which contains the absorbed excess alkanol, from a preceding cycle of the process. On passage through the absorber layer 5, the starting stream becomes charged with this alkanol and is fed into the reactor 1 as stream 8. The alkanol consumed in the etherification is supplemented by admixture with stream 8 before it enters the reactor as stream 9.

It is of course possible to alter the variant shown as an example in FIG. 1 so that the etherification catalyst is present in only one reactor. In this case, the etherification is carried out completely in this one reactor, and a part of the reaction mixture leaving this reactor is recycled as a dilution of the starting stream, if desired via a condenser, to this one etherification reactor, and only a part of the completely etherified reaction mixture is fed to the absorber layer 4 for the removal of alkanol. Instead of a fixed-bed reactor, it is of course also possible to employ a tubular reactor for the etherification, in which reactor a cooling medium flowing around the tube conducts away the heat of reaction.

After extensive charging of the absorber layer 4 with the alkanol to be removed, the function of the absorber layer 4 and 5 is then exchanged, by switching the valves above and below the absorber layers 4 and 5, so that 5 is now used for removal of alkanol from the ready reaction mixture, and 4 is now used for releasing absorbed alkanol to the starting gas mixture. For this purpose, valves are positioned above and below 4 and 5, of which valves, those represented as black in FIG. 1 are closed and those represented as white in FIG. 1 are open. When the function of 4 and 5 are switched over, the previously closed valves are then open and the previously open valves are closed. This can occur, for example, automatically and simultaneously, in a manner which is known to one skilled in the art, so that there is no interruption, or only minimum interruption, in a continuous operation. This automatic actuation of the valves can be controlled in a manner which is likewise known to one skilled in the art, for example by the monitoring of the alkanol concentration in stream 12 emerging from the absorber layer. This alkanol concentration which is used to control the valves can be made dependent on the desired specification, that is to say the highest alkanol concentration permitted in the end products. As already described above, in the case of high requirements of freedom from alkanol of the end products, a safety absorber filter can be connected downstream to the absorber layer used for the absorption, which filter can be included in the absorption and desorption cycle in the manner which has likewise been described above.

It is of course also possible to carry out the distillation in debutanizing column 6, represented in FIG. 1 as a one-stage process, as a multi-stage process, if the position of the boiling points of the alkyl tert.-alkyl ether to be obtained and the residual raffinate to be obtained make this necessary.

Figure 2:
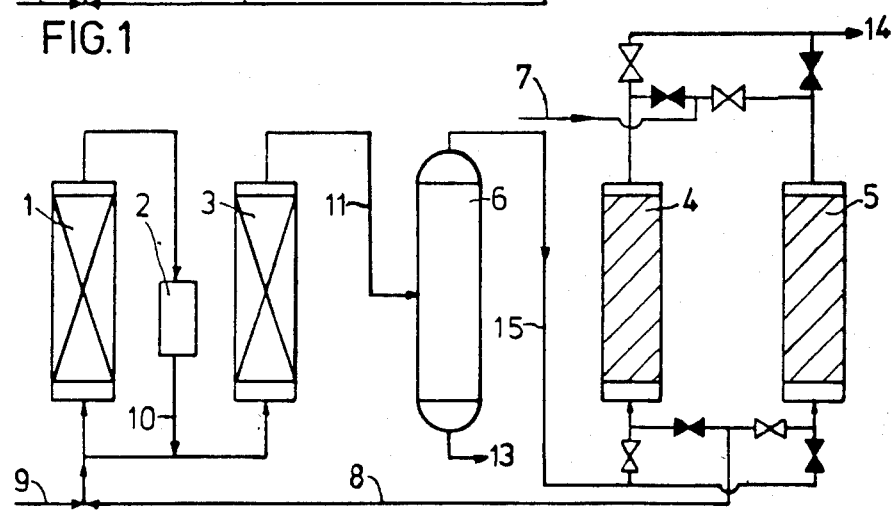

FIG. 2 shows a further possible variant of the process according to the invention. The meaning of positions 1 to 14 is the same in FIG. 2 as in FIG. 1. Whilst the process variant shown in FIG. 1 had the sequence etherification reaction/alkanol removal/distillation, in FIG. 2 the course of the process represented is etherification reaction/distillation/alkanol removal. The reaction mixture emerging from the after-reactor 3 and largely freed from tert.-olefin thus initially enters the debutanizing column 6 in which the desired alkyl tert.-alkyl ether is produced as the bottom product 13 and the residual mixture 15, which passes over at the top, is freed from ether, but still contains alkanol, is obtained; this residual mixture, after condensation to the liquid phase, is then converted in the absorber layer 4, as already described further above, into the alkanol-free residual raffinate 14.

Of course, all the variations already mentioned above, concerning the replacement of the fixed-bed etherification reactors 1 and 3 by only one fixed-bed reactor or by a tubular reactor, and also the replacement of the one-stage distillation in the debutanizing column 6 by multi-stage distillation, and the supplementation of absorber 4, arranged for absorption, by a downstream safety absorption filter, also apply to the process variant represented in FIG. 2. In particular, the following variation can be applied to the distillation stage in the debutanizing column 6: in the case of relatively high alkanol excess within the limits of the range given above, the distillation can be arranged such that the emerging alkyl tert.-alkyl ether 13 contains a small amount of alkanol. This variant is particularly useful when the ether is to be used as a solvent or extracting agent and provided this is required by the specification to be adhered to with respect to the alkanol concentration. However, the distillation can also be carried out such that the total alkanol is distilled off via the top, together with the residual hydrocarbons. In this variant of the process according to the invention, it is advantageous to establish the amount of alkanol at about 1.1 to 1.2 mols per mol of tert.-olefin to be reacted.

The switch over of the absorber layers 4 and 5 represented in FIG. 2 from absorption to desorption and vice versa occurs in the same manner as described in connection with FIG. 1.

The starting material 7, the starting material 8 charged with alkanol, the alkanol feed 9 and the circulating stream 10 for controlling the heat of reaction also correspond completely to the description given for FIG. 1.

Figure 3:
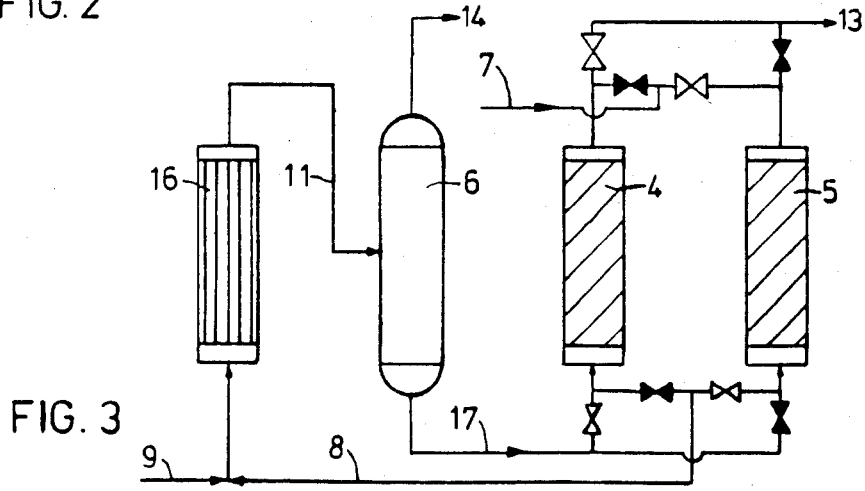

In FIG. 3, the reaction variant is again shown with the sequence etherification reaction/distillation/alkanol removal, but in this case, for example, for a tubular reactor 16 in which the etherification is operated at a relatively high alkanol excess. The reaction stream emerging from the reaction and largely freed from tert.-olefin is separated in the debutanizing column 6 such that the bulk of the excess alkanol occurs together with the desired alkyl tert.-alkyl ether in bottom product 17, which is now passed in an analogous manner, as already described above, over the absorber layer 4 for the removal of alkanol and production of an alkanol-free ether 13. The switching of the two absorber layers 4 and 5 and the associated valves above and below these absorber layers takes place in the manner described above. An amount of 1.2 to 6 mols of alkanol per mol of tert.-olefin may be mentioned as an example of the amount of alkanol for this variant. In addition to occurring in the bottom product 17 of the debutanizing column 6, alkanol also occurs in the top product 14 in an order of magnitude of approx. 0.5 to 10% by weight. If the alkanol content is an interfering factor in this hydrocarbon raffinate, it is possible, in a manner similar to that shown in FIG. 2, also to pass the top product through an absorber layer, which, of course, is included in the desorption by the starting gas stream. In this case, both the bottom product and the top product of the distillation are thus passed over one absorption layer each.

Of course, when higher requirements of purity apply, the ether which is always produced as the bottom product in the distillation can be subjected to a further precision distillation, the ether being taken off as the top product.

The etherification reaction is effected in one of the reactor types mentioned, in a known manner, on an acidic cation exchanger, for example a styrene/divinylbenzene polymer, containing sulphonic acid groups, in a fixed or suspended layer, at a temperature of 30° to 120° C., preferably 40° to 90° C., and a pressure of 1 to 50 bar, preferably 3 to 20 bar, with a catalyst throughput per hour (WHSV = weight hourly space velocity) of 0.1 to 15 kg of total starting materials per kg of cation exchanger per hour.

The following may be mentioned as examples of pure alkyl tert.-alkyl ethers which can be prepared according to the invention: methyl tert.-butyl ether (MTBE), ethyl tert.-butyl ether, propyl tert.-butyl ether, butyl tert.-butyl ether, hexyl tert.-butyl ether, octyl tert.-butyl ether, tert.-amyl methyl ether (TAME), tert.-amyl ethyl ether, tert.-amyl butyl ether, tert.-amyl octyl ether, methyl tert.-hexyl ether, ethyl tert.-hexyl ether, methyl tert.-octyl ether and ethyl tert.-octyl ether.

Such alkyl tert.-alkyl ethers contain residual alkanol in an amount below 0.5% by weight, for example <0.01 to 0.5% by weight, preferably 0.01 to 0.26% by weight. If, as described above, a particular residual alkanol content is desired in the alkyl tert.-alkyl ether, this can be obtained in the manner described above.

The hydrocarbon raffinates obtained are mixtures which, by use of the process according to the invention, are largely free of tert.-olefins, but otherwise correspond to the starting hydrocarbon mixtures. The residual content of tert.-olefins is below 8% by weight, for example 0.1 to 6% by weight, preferably 0.5 to 4% by weight. The content of residual alkanol has the values mentioned for the ethers.

For the separation of the reaction mixture obtained in the etherification reaction, the process according to the invention permits the use of absorptive working-up stages, combined with only one distillation stage which is in general very simple to carry out, instead of conventional multi-stage distillation stages in possibly multi-tray columns. This produces great savings with respect to capital costs and energy costs.

It is surprising that, on the one hand, the alkanols employed in excess for etherification are so firmly held on the absorber resins which can be employed according to the invention that, even in the case of relatively high throughputs through the absorber layers, within the ranges given, "penetration" of the alkanol can be prevented, so that "on specification" ethers and residual gases can be obtained. On the other hand, in the light of the literature quoted at the outset, it is surprising that the absorbed alkanol can be removed without drastic methods of treatment, such as steaming out or drying in vacuo at temperatures above 100° C., and that, rather, this removal is effected with the aid of the starting stream of the reaction, so that the absorption and desorption of the alkanols can be combined in a continuous process by simple switching of the absorber layers.

Since the desorption of the alkanol is promoted by the tertiary olefins of the flushing stream, the desorption may even be effected at the absorption temperature, so that the regenerative methanol removal can be carried out at a given temperature level, almost without requirement of energy.

EXAMPLE 1

A thermostatic continuous flow reactor with an internal diameter of 20 mm was filled with a macroporous styrene/divinylbenzene polymer, in the $H^+$ form, containing sulphonic acid groups (with 18% of divinylbenzene cross-linked; total capacity 1.4 equivalents/l; commercial product Lewatit SPC 118 of Bayer AG), the amount of which with respect to the amount of starting material to be employed is proportioned such that a catalyst throughput of WHSV = 1 (weight hourly space velocity) is attained. The temperature control is effected via temperature-measuring points which are located at intervals of 100 mm each in the reaction tube. 100 g of $C_4$ raffinate I/hour (see Table I) and 26.95 g of methanol/hour, after passing through a mixing chamber, were passed over the catalyst at a reaction temperature of 40° C. and a reaction pressure of 15 bar, regulated via a pressure controller. The reaction product leaving the reactor was stored temporarily in a cooled separator. The gas chromatographically determined composition of the starting stream and product stream are represented in Table I.

TABLE I

|  | Starting stream (% by weight) | Product stream (% by weight) |
|---|---|---|
| i-Butene | 37.2 | 0.7 |
| n-Butene | 32.4 | 31.9 |
| Butane | 9.2 | 9.2 |
| Methanol | 21.2 | 0.9 |
| MTBE (methyl tert.-butyl ether) | — | 55.8 |
| Oligomers etc. | — | 1.5 |
| Conversion of i-butene 98.1%. | | |

EXAMPLE 2

The removal of methanol from the product stream of Example 1 is effected via 2 tubular steel reactors operated alternately and having an internal diameter of 25 mm and a total volume of 250 ml. The reactors have outer jackets, through which water circulates via a thermostat. Furthermore, they are provided with temperature-measuring points. The pressure is regulated to 5 bar via a pressure controller. The product stream is metered in upwards from below, via a diaphragm piston pump. Instantaneous and average samples are withdrawn at the exit of the reactor and investigated by gas chromatography. The reactors which are operated alternately are filled with 120 ml each of dried, macroporous, slightly basic styrene/divinylbenzene resin containing dimethylbenzylamine groups (commercial product Lewatit MP 62 of Bayer AG) ($\triangleq$100 g of water-moist resin).

For the absorption of methanol, 1.2 l/hour of the product stream from Example 1 ($\triangleq$840 g/hour) with a methanol content of 0.9% by weight are passed in upwards, from below, over one of the two absorbers. The temperature is kept at 20° C. in this process. The absorption effects and their development over a period of 5 hours are represented in Table II.

TABLE II

| t (hour) | Charge (g) | Methanol in the eluate (% by weight) |
|---|---|---|
| 0.5 | 420 | 0.1 |
| 1 | 840 | 0.1 |
| 2 | 1,680 | 0.1 |
| 3 | 2,520 | 0.1 |
| 4 | 3,360 | 0.2 |
| 4.5 | 3,780 | 0.4 |
| 5 | 4,200 | 0.7 |

After 5 hours, the product stream from Example 1 is switched over to the 2nd absorber, whilst the 1st absorber is flushed from bottom to top with 1.2 l/hour of $C_4$-raffinate I ($\hat{=}$ 840 g/hour) at 50° C. and 6 bar. The flushing stream has the following composition:
i-butene: 47.2% by weight
n-butenes: 41.1% by weight and
butanes: 11.7% by weight The desorption effects of the flushing process are represented in Table III below.

TABLE III

| t (hour) | Flushing stream (g) | Methanol in the eluate (% by weight) |
|---|---|---|
| 0.5 | 420 | 2.5 |
| 1.5 | 1,260 | 1.4 |
| 2.5 | 2,100 | 0.1 |

The flushing stream charged with methanol from the desorption process is then fed to the etherification reactor, after being supplemented by the amount of methanol required for the reaction. After about 5 hours, the two absorption reactors are again switched over, and are further operated continuously in this alternating mode. The product stream after the absorption, which stream has largely been freed from methanol, is passed into a pressure distillation column, in which, at approx. 5 bar, the residual $C_4$ hydrocarbons are obtained via the top as raffinate II having a methanol content of 0.2% by weight, and a 97% strength by weight methyl tert.-butyl ether (MTBE) containing proportions of about 2.5% by weight of $C_4$ oligomers is obtained at the bottom.

EXAMPLE 3

The product stream from Example 1 is passed into a pressure distillation column in which, at about 5 bar, the residual $C_4$-hydrocarbons are obtained via the top as raffinate II with a methanol content of 2.1% by weight, and a 97% strength by weight MTBE containing 2.5% by weight of oligomer constituents is obtained at the bottom.

The top stream of the distillation stage is fed to the continuous absorptive removal of methanol in the apparatus described below:

The absorption apparatus consists of two thermostatic doubled-walled reactors which are connected in parallel, intended for alternate operation, have a length of 140 cm and an internal diameter of 25 mm, and are each charged with 680 cm$^{-3}$ of a methanol-moist macroporous, slightly basic styrene/divinylbenzene resin containing dimethylbenzylamine groups (commercial product MP 62 of Bayer AG) in bead form (diameter from 0.3 to 1.5 mm). Both reactors are connected together by a system of pipelines such that absorption of methanol, at 5 bar and 22° C., from a $C_4$-hydrocarbon stream (raffinate II) is possible on the one hand, and desorption of the methanol present on the absorber resin by means of a methanol-free $C_4$-hydrocarbon stream (raffinate I) at 50° C. and 20 bar is possible on the other hand, and switching over to the reverse procedure in each case can then be effected. The methanol contents of the absorption stream and of the desorption stream are monitored via a continuously operated gas chromatograph. Since the absorber resin is employed in the methanol-containing form, the flushing stream, consisting of the $C_4$-raffinate I (i-butene 47.2% by weight, n-butenes 41.1% by weight and butanes 11.7% by weight) is first passed over the absorber resin to desorb the methanol. The desorption is operated at 50° C. and 20 bar, at a rate of 1,250 ml of the flushing stream/hour. The $C_4$ raffinate I leaving the desorption reactor initially has a methanol content greater than 5% by weight, which decreases in the course of the first hour to 0.1% by weight. After 1½ hours including a heating time of ½ hour, the desorption of the first absorber resin layer is completed. After the flushing stream has been switched over to the second absorber resin layer, a product stream, which was obtained analogously to Example 1, is passed over the first absorber resin layer for removal of methanol. This product stream has the following composition:
i-butene: 1.6% by weight
n-butenes: 74.7% by weight
butanes: 21.5% by weight
methanol: 2.1% by weight
residue: 0.1% by weight 750 ml per hour of this product stream are passed over the absorber resin layer, at 22° C. and 5 bar. The $C_4$-raffinate II leaving the absorption reactor contains less than 0.1% by weight of methanol after a period of 2½ hours, and reaches a methanol content of 1% by weight only after 3 hours. Thereafter, the flushing stream and the raffinate II stream are switched over to the two absorption reactors. These switching operations are continued in a 3-hour cycle over a period of 20 days, without the absorption effects changing. In this process, the following $C_4$-raffinate II specification is attained:
i-butene: 1.7% by weight
n-butenes: 76.2% by weight
butanes: 21.9% by weight
methanol: 0.1% by weight
residue: 0.1% by weight

EXAMPLE 4

Two successively connected tubular reactors with an internal diameter of 20 mm are filled with 140 g each of a macroporous acid styrene/divinylbenzene cation exchanger resin containing sulphonic acid groups, as in Example 1. A product-recycling branch is arranged between the two reactors, so that, by adjusting a release valve and with the aid of a pump, a part of the product stream can be recycled to the reactor entrance of the first reactor tube, after passing through a condenser. The temperature control is effected via temperature-measuring points which are arranged at intervals of 100 mm each in the reaction tube. When the recycling ratio is adjusted to be 2:1 (recycling to fresh input), 100 g/hour of $C_4$-raffinate I and 40 g/hour of methanol are brought to reaction at 40° to 70° C. in the first reactor, and at 40° C. in the second reactor. The compositions of the starting stream and the product stream are represented in Table IV below.

TABLE IV

| | Starting stream (% by weight) | Product stream (% by weight) |
|---|---|---|
| i-Butene | 33.7 | 0.3 |
| n-Butenes | 29.4 | 29.0 |
| Butanes | 8.4 | 8.4 |
| Methanol | 28.5 | 9.8 |
| MTBE | — | 51.4 |
| Oligomers etc. | — | 1.1 |
| Conversion: 99.1% of the i-butene. | | |

EXAMPLE 5

The product stream from Example 4 is passed into a pressure distillation column in which, at about 5 bar, the residual $C_4$-hydrocarbons containing about 2.5% by weight of methanol are obtained via the top as raffinate II, and an 83.8% strength by weight MTBE containing 14.4% by weight of methanol and about 1.8% by weight of oligomer constituents is obtained at the bottom. This bottom stream is passed, at 25° C. and at a WHSV (weight hourly space velocity) of 5, relative to dry absorber resin, over 30 g of an absorber resin layer consisting of the ion exchanger employed in Examples 2 and 3. The experimental arrangement corresponds to that in Example 2. At the exit of the absorber resin layer, a substance stream is obtained which has the following composition according to gas chromatographic analysis:
MTBE: 96.8% by weight
methanol: 0.9% by weight
undetermined residue: 2.3% by weight After 1½ hours, the charging stream (the bottom product) is switched to the second absorber resin layer. The desorption of the methanol from the first absorber resin layer is effected according to the conditions given in Example 2. The absorption/desorption cycle was repeated several times.

EXAMPLE 6

In the apparatus described in Example 1, 100 g/hour of a partially hydrogenated $C_5$-hydrocarbon stream from a thermal cracker (light ends before aromatics) containing 20% by weight of isoamylenes, and 8.6 g/hour of methanol are brought to reaction on 110 g of a strongly acid, macroporous cation exchanger doped with elementary palladium (0.75 g of Pd per liter of cation exchanger) at 70° C. and 10 bar. Gas chromatographic investigation of the product stream gives the following composition:
i-amylenes: 4.1% by weight
TAME (tert.-amyl methyl ether): 20.9% by weight
methanol: 1.2% by weight
residual $C_5$ hydrocarbons: 72.1% by weight
higher ethers + hydrocarbons: 1.7% by weight
Conversion of the i-amylenes: 78% by weight.

EXAMPLE 7

The product stream from Example 6 is fed to a distillation column, in which TAME having a purity of 95% by weight and containing 5% by weight of higher ethers and hydrocarbons is obtained as a side stream of the column, and the residual $C_5$-hydrocarbons containing 1.6% by weight of methanol are obtained as the top product. This top stream is passed, at 25° C. and at a WHSV of 20, relative to dry absorber resin, over 15 g of the ion exchanger employed in Examples 2, 3 and 5. The apparatus is the same as in Example 2. The composition of the distillation top stream at the exit of the absorber resin is analysed gas chromatographically after defined periods. The absorption effects and their development over a period of 3½ hours are represented in Table V.

TABLE V

| Charge: | |
|---|---|
| $C_5$ hydrocarbons | 97.9% by weight |
| methanol | 1.6% by weight |
| TAME | 0.5% by weight |

| Absorption effect over 3.5 hours: | |
|---|---|
| t (hour) | Methanol in the eluate (% by weight) |
| 0.5 | 0.1 |
| 1.0 | 0.1 |
| 1.5 | 0.1 |
| 2.0 | 0.1 |
| 2.5 | 0.1 |
| 3.0 | 0.1 |
| 3.5 | 0.2 |

The charging stream is then switched over to the second absorber layer. The methanol desorption from the first absorber layer is effected according to the conditions given in Example 2. The absorption/desorption cycle is repeated five times, without the capacity for taking up methanol decreasing.

EXAMPLE 8

In the apparatus described in Example 1, 100 g/hour of a partially hydrogenated $C_5$ hydrocarbon stream from a thermal cracker (light ends before aromatics) containing 50% by weight of isoamylene, and 12.4 g/hour of ethanol are brought to reaction on a strongly acid, macroporous cation exchanger doped with palladium (0.75 g of Pd per liter of resin), at 70° C. and 10 bar. Gas chromatographic investigation of the product stream gives the following composition:
i-amylenes: 4.4% by weight
TAEE (tert.-amyl ethyl ether): 22.2% by weight
ethanol: 2.6% by weight
residual $C_5$ hydrocarbons: 69.0% by weight
higher ethers + hydrocarbons 1.8% by weight
Conversion of the i-amylenes: 75%.

This product stream is passed, at 25° C. and at a WHSV of 20, relative to dry absorber resin, over 15 g of the ion exchanger employed in Examples 2, 3, 5 and 7. The apparatus described in Example 2 is used.

The composition of the exit stream from the absorber is analysed gas chromatographically after defined periods. The absorption effects and their development over a period of 3½ hours are represented in Table VI.

TABLE VI

| t (hour) | Ethanol in the eluate (% by weight) |
|---|---|
| 0.5 | 0.1 |
| 1.0 | 0.1 |
| 1.5 | 0.1 |
| 2.0 | 0.1 |
| 2.5 | 0.1 |
| 3.0 | 0.2 |
| 3.5 | 0.5 |

The charging stream is then switched over to the 2nd absorber resin layer. The desorption of the ethanol from the 1st absorber resin layer is effected according to the conditions given in Example 2. The absorption/desorption cycle is repeated five times, without the capacity for taking up ethanol decreasing.

EXAMPLE 9 (Preparation of a cation exchanger doped with palladium)

A macroporous cation exchanger was prepared according to German Pat. No. 1,113,570, Example 3. The water-moist H+ form of this cation exchanger was supplied, in a batch, with an amount of palladium acetate such that 0.75 g of palladium per liter of dry resin was present on the cation exchanger after reduction with hydrogen. The acid liberated during the treatment with palladium acetate was neutralized with 1% strength by weight sodium hydroxide solution. The cation exchanger, washed neutral, was then dried for 24 hours at 100° C. in the vacuum from a water-jet pump. The palladium present on the cation exchanger was then reduced to the metal using hydrogen, and between 90° and 100° C. under a pressure of 20 to 25 bar, in the course of 48 hours.

EXAMPLE 10–18

In the absorption apparatus described in Example 2, the C5-hydrocarbon stream, which was obtained as the top product of the distillation carried out in Example 7, was passed over the absorber resins given below, to remove methanol. The C5-starting stream from Example 6 was used for desorption.

Table V represents the absorption effects and desorption effects at the various absorber resins, which effects were determined via gas chromatographic measurements.

The ion exchangers employed in the examples are:
Example 10: SC 102, strongly acid, gelatinous, cross-linked styrene/divinylbenzene resin containing sulphonic acid groups, in the Na+ form. Example 11: CNP 80, macroporous, slightly acid cation exchanger of the acrylic acid type with special crosslinking. Example 12: DN H+, condensation resin based on phenol/formaldehyde containing sulphonic acid groups. Example 13: SPC 118, like SC 102, but macroporous. Example 14: MP 62, macroporous, slightly basic styrene/divinylbenzene resin containing dimethylbenzylamine groups. Example 15: MP 500, strongly basic, macroporous styrene/divinylbenzene resin of type I. Example 16: MP 504, strongly basic, gelatinous styrene/divinylbenzene resin of type I. Example 17: M 600, strongly basic gelatinous styrene/divinylbenzene resin of type II. Example 18: XAD 12 styrene/divinylbenzene ion exchanger containing N-oxide groups.

The resins of Examples 10–17 are commercial products of Bayer AG, and the resin of Example 18 is a commercial product of the Rohm and Haas Company.

TABLE V

| Charging stream: | | C5-hydrocarbon stream + 2% of methanol; | | | | T = 25°, p = 1 bar; LHSV = 5 (liquid hourly space velocity) | | | |
|---|---|---|---|---|---|---|---|---|---|
| Flushing stream: | | C5-hydrocarbon stream; | | | | T = 35°, p = 1 bar; LHSV = 5 | | | |
| Amounts: | | A = 630 g; B = 1,260 g; C = 1,890 g | | | | | | | |
| Example | | 10 | 11 | 12 | 13 | 14 | 15 | 16 | 17 | 18 |
| Absorbent | | SC 102 | CNP 80 | DNH+ | SPC 118 | MP 62 | MP 500 | MP 504 | M 600 | XAD 12 |
| Methanol concentration in the eluate | | % by weight | % by weight | % by weight | % by weight | % by weight | % by weight | % by weight | % by weight | % by weight |
| Absorption | B | 0.1 | 0.4 | 0.5 | 0.7 | 0.1 | 0.3 | 0.4 | 0.8 | 0.1 |
| Desorption | A | 4.2 | 2.8 | 1.9 | 2.1 | 3.4 | 2.7 | 2.4 | 1.7 | 2.8 |
| | B | 2.7 | 1.6 | 1.2 | 0.9 | 1.9 | 0.9 | 0.9 | 0.8 | 1.3 |
| | C | 0.5 | 0.3 | 0.2 | 0.1 | 0.5 | 0.3 | 0.2 | 0.3 | 0.4 |
| Absorption | A | 0.1 | 0.4 | 0.3 | 0.4 | 0.1 | 0.1 | 0.2 | 0.4 | 0.1 |
| | B | 0.1 | 0.6 | 0.5 | 0.6 | 0.1 | 0.4 | 0.4 | 0.7 | 0.1 |
| | C | 0.4 | 0.8 | 0.7 | 1.0 | 0.1 | 1.0 | 0.9 | 1.2 | 0.1 |
| Desorption | A | 4.1 | 3.7 | 2.0 | 1.8 | 3.8 | 3.0 | 2.5 | 1.4 | 2.8 |
| | B | 2.4 | 1.5 | 1.1 | 0.6 | 2.6 | 1.7 | 0.8 | 0.5 | 1.0 |
| | C | 0.7 | 0.4 | 0.3 | 0.3 | 0.5 | 0.5 | 0.3 | 0.2 | 0.5 |
| Absorption | A | 0.1 | 0.5 | 0.4 | 0.6 | 0.1 | 0.1 | 0.2 | 0.4 | 0.1 |
| | B | 0.4 | 0.8 | 0.9 | 0.8 | 0.1 | 0.5 | 0.7 | 1.0 | 0.1 |
| | C | 0.6 | 1.0 | 1.1 | 1.2 | 0.2 | 0.8 | 1.0 | 1.2 | 0.3 |

What is claimed is:

1. A process for the preparation of pure alkyl tertiary alkyl ethers and hydrocarbon raffinates which are substantially free from tertiary olefins and alkanols which comprises:
   (a) contacting an alkanol and a hydrocarbon mixture containing at least one tertiary olefin in a reaction zone, said alkanol being present in a stoichiometric excess;
   (b) removing the reaction product from the reaction zone and absorbing excess alkanol in said reaction product or a partial stream thereof by absorption on a synthetic ion exchanger containing groups which exchange cations or anions or mixture of such ion exchangers, said absorbing conducted in the liquid phase;
   (c) following absorption of at least a portion of said alkanol on said synthetic ion exchanger, desorbing said alkanol by contacting the same with feed hydrocarbon mixture containing at least one tertiary olefin, said desorbing conducted in the liquid phase.

2. A process according to claim 1, wherein the desorbed alkanol in admixture with said hydrocarbon mixture containing at least one tertiary olefin is thereafter charged to a reaction zone wherein said alkanol is reacted with said tertiary olefin, said reaction zone containing said alkanol in stoichiometric excess.

3. A process according to claim 2, wherein said desorbed alkanol and said hydrocarbon mixture containing at least tertiary olefin are recycled to the reaction zone from which unre-acted alkanol was removed and absorbed on said synthetic ion exchanger.

4. A process according to claim 1, wherein said tertiary olefin is reacted with said alkanol on an acid cation exchanger.

5. A process according to claim 1, wherein absorption is carried out at 0° to 60° C. under a pressure of 0.1 to 20 bars.

6. A process according to claim 1, wherein desorption is carried out at 20° to 100° C. under a pressure of 3 to 30 bars.

7. A process according to claim 6, wherein said desorption is carried out at a pressure of 5 to 15 bars.

8. A process according to claim 2, wherein absorption is carried out at 0° to 60° C. under a pressure of 0.1 to 20 bars and desorption is carried out at 20° to 100° C. under a pressure of 3 to 30 bars.

9. A process according to claim 1, wherein said synthetic ion exchanger is in the form of at least 2 divided layers, a first divided layer of which is employed for absorption of alkanol, a second divided layer of which is employed thereafter for alkanol absorption when said first divided layer is undergoing desorption of previously absorbed alkanol and said second divided layer is thereafter desorbed of its absorbed alkanol while said first divided layer is again employed for alkanol absorption.

10. A process according to claim 1, wherein the rate of desorption is adjusted to 0.5 to ten times the value of the rate of absorption.

11. A process according to claim 9, wherein the absorption layer and the desorption layer are charged with a weight hourly space velocity (WHSV) of 0.1 to 100 kg of reaction mixture per kg of synthetic ion exchanger per hour.

12. A process according to claim 11, wherein a higher weight hourly space velocity is established for desorption than is employed for absorption.

13. A process according to claim 1, wherein the alkanol concentration, relative to the entire composition undergoing absorption, is 0.01 to 90% by weight.

14. A process according to claim 1, wherein the reaction mixture leaving the reaction zone is initially freed, on an absorber resin, of excess alcohol and is thereafter separated into alkyl tertiary alkyl ether and residual gas by distillation, at least one partial stream obtained by distillation containing an alkanol is thereafter treated to remove alkanol thereof by adsorption on said synthetic ion exchanger.

15. A process according to claim 1, wherein said synthetic ion exchanger comprises a styrene/divinylbenzene resin containing a sulphonic acid group in the free acid or sodium form.

16. A process according to claim 1, wherein said synthetic ion exchanger comprises a styrene/divinylbenzene resin containing dimethylbenzyl amino groups.

17. A process according to claim 1, wherein said synthetic ion exchanger comprises a macroporous cation exchanger doped with elementary palladium.

18. A process according to claim 1, wherein the synthetic cation exchanger comprises a strongly basic gelatinous styrene/divinylbenzene resin.

19. A process according to claim 1, wherein said synthetic ion exchanger comprises a condensation resin based on phenol/formaldehyde containing sulfonic acid groups.

20. A process according to claim 1, wherein said synthetic ion exchanger comprises a macroporous slightly acid cation exchanger of the acrylic acid type which has been cross-linked.

21. A process according to claim 1, wherein said synthetic ion exchanger comprises a styrene/divinylbenzene ion exchanger containing N-oxide groups.

22. A process according to claim 1, wherein desorption is carried out at 30° to 60° C.

23. A process according to claim 1, wherein desorption is carried out with the same hydrocarbon mixture containing at least one tertiary olefin that is directed to the reaction zone.

24. A process according to claim 1, wherein said absorption is conducted in a first column and said desorption is conducted in a second column, said first column and said second column being parallel thereto.

* * * * *

UNITED STATES PATENT AND TRADEMARK OFFICE
CERTIFICATE OF CORRECTION

PATENT NO. : 4,504,688

DATED : March 12, 1985

INVENTOR(S) : Jens Herwig, et al.

It is certified that error appears in the above-identified patent and that said Letters Patent is hereby corrected as shown below:

1st Page, under "U.S. Patent Documents
Col. 2, line 4
Col. 5, lines 35, 36
Col. 11, line 61

1st line delete "3,021,274" and substitute --3,021,374--
Correct spelling of "azeotropes"
Correct spelling of "procedure"
Delete "$cm^{-3}$" and substitute --$cm^3$--

Col. 15, Table V, 1st column, line 5

Delete "Absorbent" and substitute --Adsorbent--

Signed and Sealed this

Twentieth Day of August 1985

[SEAL]

Attest:

DONALD J. QUIGG

Attesting Officer

Acting Commissioner of Patents and Trademarks